(12) United States Patent
Tillett et al.

(10) Patent No.: US 12,239,390 B2
(45) Date of Patent: Mar. 4, 2025

(54) METHOD AND APPARATUS FOR ATTACHING A REFERENCE MARKER TO A PATIENT

(71) Applicant: Mobius Imaging, LLC, Shirley, MA (US)

(72) Inventors: Jason Tillett, Shirley, MA (US); Scott Coppen, Amesbury, MA (US)

(73) Assignee: Mobius Imaging, LLC, Shirley, MA (US)

( * ) Notice: Subject to any disclaimer, the term of this patent is extended or adjusted under 35 U.S.C. 154(b) by 0 days.

(21) Appl. No.: 18/135,861

(22) Filed: Apr. 18, 2023

(65) Prior Publication Data
US 2023/0248445 A1 Aug. 10, 2023

Related U.S. Application Data

(63) Continuation of application No. 16/605,712, filed as application No. PCT/US2018/046044 on Aug. 9, 2018, now Pat. No. 11,660,145.
(Continued)

(51) Int. Cl.
*A61B 34/20* (2016.01)
*A61B 10/02* (2006.01)
(Continued)

(52) U.S. Cl.
CPC ............ *A61B 34/20* (2016.02); *A61B 10/025* (2013.01); *A61B 90/39* (2016.02);
(Continued)

(58) Field of Classification Search
CPC ...................................................... A61B 34/20
See application file for complete search history.

(56) References Cited

U.S. PATENT DOCUMENTS

| 5,490,852 A | 2/1996 | Azer et al. |
| 5,575,794 A | 11/1996 | Walus et al. |

(Continued)

FOREIGN PATENT DOCUMENTS

| CN | 201422918 Y | 3/2010 |
| CN | 201542641 U | 8/2010 |

(Continued)

OTHER PUBLICATIONS

English language abstract and machine-assisted English translation for CN 101579269 extracted from espacenet.com database on Jan. 9, 2020, 8 pages.

(Continued)

*Primary Examiner* — Christian A Sevilla
(74) *Attorney, Agent, or Firm* — Howard & Howard Attorneys PLLC (57) ABSTRACT

Systems and methods for attaching a reference marker to a patient in a computer-assisted image-guided surgery system. An apparatus for attaching a reference marker to a patient includes an elongated member extending between a first end and a second end, a sharp tip located proximate to the first end of the elongated member that is configured to break through a cortical surface of a bone of the patient to enable the elongated member to be advanced into the bone, an anchoring device that is extendable from the elongated member in order to anchor the apparatus within the bone and inhibit relative movement of the apparatus and the bone, and a reference marker device comprising at least one optical marker configured to enable the apparatus to be tracked using a motion tracking system.

18 Claims, 7 Drawing Sheets

Related U.S. Application Data (60) Provisional application No. 62/544,514, filed on Aug. 11, 2017.

(51) Int. Cl.
*A61B 90/00* (2016.01)
*A61B 17/00* (2006.01)
*A61B 34/30* (2016.01)

(52) U.S. Cl.
CPC .............. *A61B 2010/0258* (2013.01); *A61B 2017/00867* (2013.01); *A61B 2034/2055* (2016.02); *A61B 34/30* (2016.02); *A61B 2090/374* (2016.02); *A61B 2090/376* (2016.02); *A61B 2090/3762* (2016.02); *A61B 2090/3764* (2016.02); *A61B 2090/3916* (2016.02); *A61B 2090/3937* (2016.02); *A61B 2090/3983* (2016.02); *A61B 2090/3991* (2016.02)

(56) References Cited

U.S. PATENT DOCUMENTS

| | | |
|---|---|---|
| 5,799,055 A | 8/1998 | Peshkin et al. |
| 5,921,992 A | 7/1999 | Costales et al. |
| 6,033,406 A | 3/2000 | Mathews |
| 6,149,592 A | 11/2000 | Yanof et al. |
| 6,226,548 B1 | 5/2001 | Foley et al. |
| 6,236,875 B1 | 5/2001 | Bucholz et al. |
| 6,275,725 B1 | 8/2001 | Cosman |
| 6,450,978 B1 | 9/2002 | Brosseau et al. |
| 6,482,178 B1 | 11/2002 | Andrews et al. |
| 6,533,455 B2 | 3/2003 | Graumann et al. |
| 6,575,899 B1 | 6/2003 | Foley et al. |
| 6,718,194 B2 | 4/2004 | Kienzle, III |
| 6,772,002 B2 | 8/2004 | Schmidt et al. |
| 6,785,572 B2 | 8/2004 | Yanof et al. |
| 6,923,817 B2 | 8/2005 | Carson et al. |
| 7,194,120 B2 | 3/2007 | Wicker et al. |
| 7,237,556 B2 | 7/2007 | Smothers et al. |
| 7,251,522 B2 | 7/2007 | Essenreiter et al. |
| 7,542,791 B2 | 6/2009 | Mire et al. |
| 7,547,307 B2 | 6/2009 | Carson et al. |
| 7,587,235 B2 | 9/2009 | Wist et al. |
| 7,699,877 B2 | 4/2010 | Davison |
| 7,722,530 B2 | 5/2010 | Davison |
| 7,751,865 B2 | 7/2010 | Jascob et al. |
| 7,787,934 B2 | 8/2010 | Mazzocchi et al. |
| 7,799,036 B2 | 9/2010 | Davison et al. |
| 7,835,784 B2 | 11/2010 | Mire et al. |
| 8,016,835 B2 | 9/2011 | Birkmeyer et al. |
| 8,046,054 B2 | 10/2011 | Kim et al. |
| 8,118,488 B2 | 2/2012 | Gregerson |
| 8,126,114 B2 | 2/2012 | Naylor et al. |
| 8,394,144 B2 | 3/2013 | Zehavi et al. |
| 8,454,583 B2 | 6/2013 | Perez-Cruet et al. |
| 8,457,790 B2 | 6/2013 | Blondel et al. |
| 8,509,503 B2 | 8/2013 | Nahum et al. |
| 8,761,337 B2 | 6/2014 | Naylor et al. |
| 8,795,188 B2 | 8/2014 | Maschke |
| 8,795,364 B2 | 8/2014 | Evans et al. |
| 8,974,460 B2 | 3/2015 | De la Fuente Klein et al. |
| 9,125,680 B2 | 9/2015 | Kostrzewski et al. |
| 9,237,861 B2 | 1/2016 | Nahum et al. |
| 9,259,282 B2 | 2/2016 | Azizian et al. |
| 9,283,048 B2 | 3/2016 | Kostrzewski et al. |
| 9,308,050 B2 | 4/2016 | Kostrzewski et al. |
| 9,545,233 B2 | 1/2017 | Sirpad et al. |
| 9,550,299 B2 | 1/2017 | Wolf et al. |
| 9,750,432 B2 | 9/2017 | Nahum et al. |
| 9,833,292 B2 | 12/2017 | Kostrzewski et al. |
| 10,004,562 B2 | 6/2018 | Kostrzewski et al. |
| 10,039,476 B2 | 8/2018 | Nahum et al. |
| 10,064,682 B2 | 9/2018 | Azizian et al. |
| 10,076,385 B2 | 9/2018 | Shoham et al. |
| 10,136,952 B2 | 11/2018 | Couture et al. |
| 10,159,534 B2 | 12/2018 | Maillet et al. |
| 2002/0107518 A1* | 8/2002 | Neubauer ............ A61B 90/39 606/54 |
| 2002/0133162 A1 | 9/2002 | Axelson et al. |
| 2003/0069591 A1 | 4/2003 | Carson et al. |
| 2004/0019263 A1* | 1/2004 | Jutras .................. A61B 90/39 600/407 |
| 2004/0030237 A1* | 2/2004 | Lee ..................... A61B 34/20 600/414 |
| 2004/0068263 A1 | 4/2004 | Chouinard et al. |
| 2004/0171930 A1* | 9/2004 | Grimm ................ A61B 90/39 606/80 |
| 2005/0085714 A1* | 4/2005 | Foley ................ A61B 17/7089 600/424 |
| 2006/0084890 A1 | 4/2006 | Block et al. |
| 2007/0156157 A1 | 7/2007 | Nahum et al. |
| 2010/0286713 A1 | 11/2010 | Melkent et al. |
| 2012/0197266 A1 | 8/2012 | Sasso |
| 2014/0003572 A1 | 1/2014 | Gregerson et al. |
| 2014/0139215 A1 | 5/2014 | Gregerson et al. |
| 2014/0249546 A1 | 9/2014 | Shvartsberg et al. |
| 2014/0265182 A1 | 9/2014 | Stanton et al. |
| 2014/0275953 A1 | 9/2014 | Gregerson et al. |
| 2014/0378985 A1 | 12/2014 | Mafi |
| 2015/0202009 A1 | 7/2015 | Nussbaumer et al. |
| 2015/0366624 A1 | 12/2015 | Kostrzewski et al. |
| 2016/0030117 A1 | 2/2016 | Mewes |
| 2016/0081754 A1 | 3/2016 | Kostrzewski et al. |
| 2016/0174914 A1 | 6/2016 | Lerch et al. |
| 2016/0220320 A1 | 8/2016 | Crawford et al. |
| 2016/0235492 A1 | 8/2016 | Morard et al. |
| 2016/0278875 A1 | 9/2016 | Crawford et al. |
| 2017/0071691 A1 | 3/2017 | Crawford et al. |
| 2017/0079727 A1 | 3/2017 | Crawford et al. |
| 2017/0172669 A1 | 6/2017 | Berkowitz et al. |
| 2017/0231702 A1 | 8/2017 | Crawford et al. |
| 2017/0239002 A1 | 8/2017 | Crawford et al. |
| 2017/0239003 A1 | 8/2017 | Crawford et al. |
| 2017/0239006 A1 | 8/2017 | Crawford et al. |
| 2017/0245951 A1 | 8/2017 | Crawford et al. |
| 2017/0252112 A1 | 9/2017 | Crawford et al. |
| 2017/0258533 A1 | 9/2017 | Crawford et al. |
| 2017/0258535 A1 | 9/2017 | Crawford et al. |
| 2017/0312039 A1 | 11/2017 | Crawford et al. |
| 2017/0348061 A1 | 12/2017 | Joshi et al. |
| 2017/0360513 A1 | 12/2017 | Amiot et al. |
| 2017/0360517 A1 | 12/2017 | Crawford et al. |
| 2018/0000546 A1 | 1/2018 | Crawford et al. |
| 2018/0110573 A1 | 4/2018 | Kostrzewski |
| 2018/0116739 A1 | 5/2018 | Gogarty et al. |
| 2018/0116740 A1 | 5/2018 | Gogarty et al. |
| 2018/0125597 A1 | 5/2018 | Gogarty et al. |
| 2018/0157238 A1 | 6/2018 | Gogarty et al. |
| 2018/0185113 A1 | 7/2018 | Gregerson et al. |
| 2018/0207794 A1 | 7/2018 | Sebring et al. |
| 2018/0221098 A1 | 8/2018 | Forsyth et al. |
| 2018/0235715 A1 | 8/2018 | Amiot et al. |
| 2018/0250077 A1 | 9/2018 | Xu et al. |
| 2018/0256259 A1 | 9/2018 | Crawford |
| 2018/0271605 A1 | 9/2018 | Kostrzewski et al. |
| 2018/0346008 A1 | 12/2018 | Nahum et al. |
| 2019/0000561 A1 | 1/2019 | Decker et al. |
| 2019/0000569 A1 | 1/2019 | Crawford et al. |
| 2019/0021795 A1 | 1/2019 | Crawford et al. |
| 2019/0021799 A1 | 1/2019 | Crawford et al. |
| 2019/0021800 A1 | 1/2019 | Crawford et al. |
| 2019/0029759 A1 | 1/2019 | Mcdonell |
| 2019/0029765 A1 | 1/2019 | Crawford et al. |
| 2019/0038362 A1 | 2/2019 | Nash et al. |
| 2019/0053859 A1 | 2/2019 | Couture et al. |
| 2019/0069961 A1 | 3/2019 | Smith et al. |
| 2019/0099222 A1 | 4/2019 | Nahum et al. |
| 2019/0117313 A1 | 4/2019 | Crawford |
| 2019/0142533 A1 | 5/2019 | Itkowitz et al. |
| 2019/0239964 A1 | 8/2019 | LeBoeuf, II et al. |

(56) References Cited

U.S. PATENT DOCUMENTS

| | | |
|---|---|---|
| 2019/0269467 A1 | 9/2019 | Forsyth et al. |
| 2019/0274765 A1 | 9/2019 | Crawford et al. |
| 2020/0155238 A1 | 5/2020 | Tillett et al. |

FOREIGN PATENT DOCUMENTS

| | | |
|---|---|---|
| CN | 101700184 B | 1/2011 |
| CN | 101579269 B | 4/2011 |
| CN | 101853333 B | 11/2012 |
| WO | 9838908 A1 | 9/1998 |
| WO | 2015115809 A1 | 8/2015 |
| WO | 2017036340 A1 | 3/2017 |
| WO | 2017122202 A1 | 7/2017 |
| WO | 2018185729 A1 | 10/2018 |

OTHER PUBLICATIONS

English language abstract and machine-assisted English translation for CN 101700184 extracted from espacenet.com database on Jan. 9, 2020, 10 pages.

English language abstract and machine-assisted English translation for CN 101853333 extracted from espacenet.com database on Jan. 9, 2020, 9 pages.

English language abstract and machine-assisted English translation for CN 201422918 extracted from espacenet.com database on Jan. 9, 2020, 7 pages.

English language abstract and machine-assisted English translation for CN 201542641 extracted from espacenet.com database on Jan. 9, 2020, 10 pages.

English language abstract and machine-assisted English translation for WO 2015/115809 extracted from espacenet.com database on Jan. 9, 2020, 8 pages.

English language abstract for WO 2017/036340 extracted from espacenet.com database on Jan. 9, 2020, 2 pages.

International Search Report from the Korean Intellectual Property Office received in related Application No. PCT/US2018/046044 dated Mar. 12, 2019.

Pal jug, Eric et al. "The JPL Serpentine Robot: a 12 DOF System for Inspection", NASA JPL Technical Reports Server, https://trs.jpl.nasa.gov/handle/2014/29159, Jan. 1, 1995, 5 pages.

Written Opinion of the International Searching Authority from the Korean Intellectual Property Office received in related Application No. PCT/US2018/046044 dated Mar. 12, 2019.

\* cited by examiner

METHOD AND APPARATUS FOR ATTACHING A REFERENCE MARKER TO A PATIENT

CROSS-REFERENCE TO RELATED APPLICATIONS

This application is a Continuation of U.S. patent application Ser. No. 16/605,712 filed on Oct. 16, 2019, which is the U.S. National Stage Entry of International Patent Application No. PCT/US2018/046044 filed on Aug. 9, 2018, which claims the benefit of priority to U.S. Provisional Patent Application No. 62/554,514 filed on Aug. 11, 2017, the disclosures of each of which are hereby incorporated by reference in their entirety.

BACKGROUND

Computer-assisted surgical procedures, which may include image guided surgery and robotic surgery, have attracted increased interest in recent years. These procedures include the integration of a "virtual" three-dimensional dataset of the patient's anatomy, typically obtained using pre-operative or intra-operative medical imaging (e.g., x-ray computed tomography (CT) or magnetic resonance (MR) imaging), to the actual position of the patient and/or other objects (e.g., surgical instruments, robotic manipulator(s) or end effector(s) in the surgical area. These procedures may be used to aid the surgeon in planning a surgical procedure and may also provide the surgeon with relevant feedback during the course of surgical procedure. There is a continuing need to improve the safety and ease-of-use of computer-assisted surgical systems.

SUMMARY

Various embodiments include systems and methods for attaching a reference marker to a patient in a computer-assisted image-guided surgery system.

Embodiments include an apparatus for attaching a reference marker to a patient includes an elongated member extending between a first end and a second end, a sharp tip located proximate to the first end of the elongated member that is configured to break through a cortical surface of a bone of the patient to enable the elongated member to be advanced into the bone, an anchoring device that is extendable from the elongated member in order to anchor the apparatus within the bone and inhibit relative movement of the apparatus and the bone, and a reference marker device comprising at least one optical marker configured to enable the apparatus to be tracked using a motion tracking system.

Further embodiments include a method of performing image guided surgery that includes inserting an apparatus comprising an elongated member having a sharp tip at an end of the elongated member into the body of a patient to cause the sharp tip to break through a cortical surface of a bone of the patient, anchoring the apparatus within the bone to inhibit relative movement of the apparatus and the bone, and tracking a reference marker device having at least one optical marker attached to the apparatus using a motion tracking system.

Further embodiments include a system for performing image guided surgery using an apparatus for attaching a reference marker to a patient.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Figure 1:
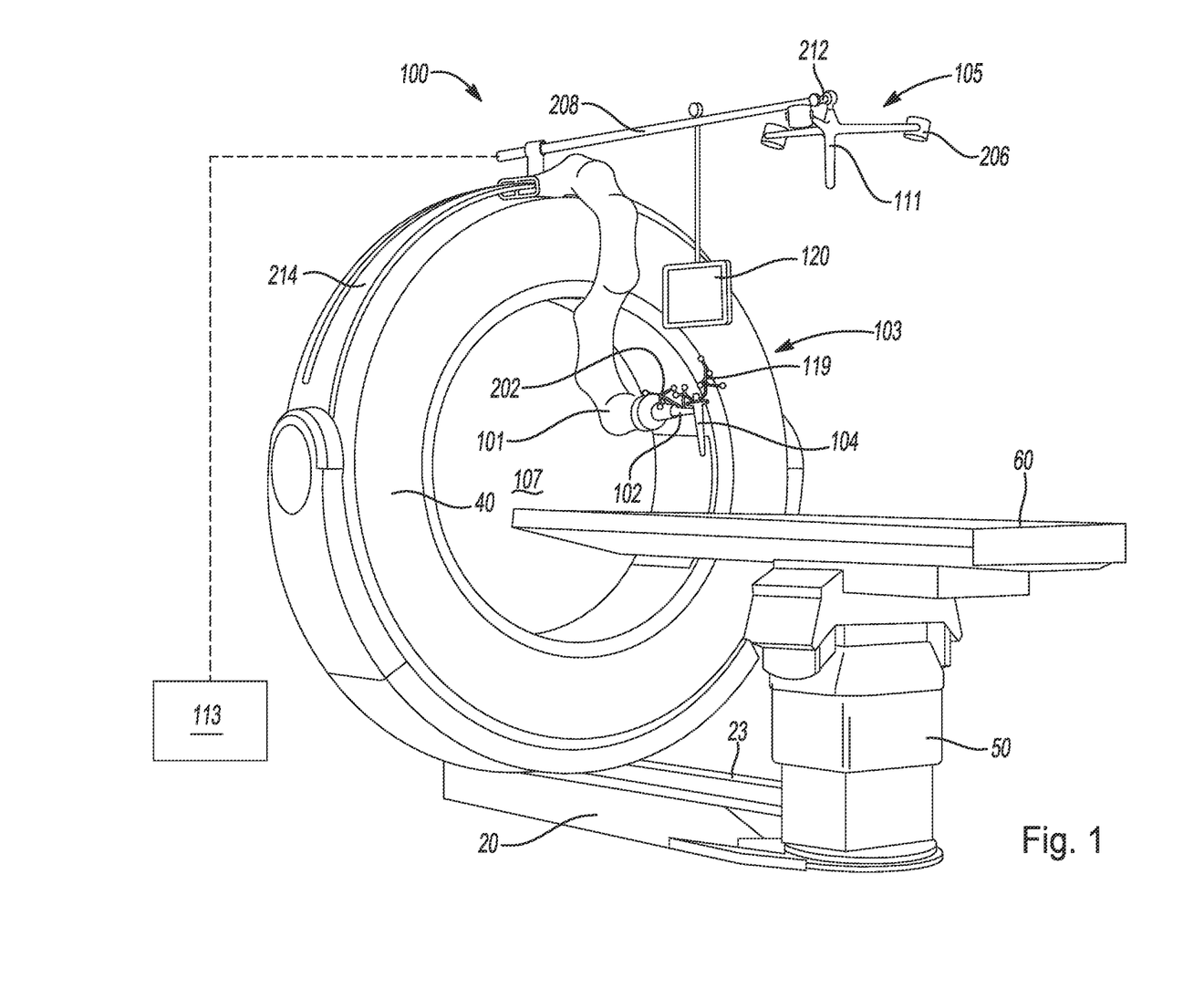
FIG. 1 is a perspective view of a system for performing robotically-assisted image-guided surgery.

FIG. 1 illustrates a system 100 for performing computer-assisted image-guided surgery according to various embodiments. The system 100 in this embodiment includes an imaging device 103, a motion tracking system 105 and a robotic arm 101 for performing a robotically-assisted surgical procedure. The robotic arm 101 may comprise a multi-joint arm that includes a plurality of linkages connected by joints having actuator(s) and optional encoder(s) to enable the linkages to rotate, bend and/or translate relative to one another in response to control signals from a robot control system. The robotic arm 101 may be fixed to a support structure at one end and may have an end effector 102 at the other end of the robotic arm 101.

The imaging device 103 may be used to obtain diagnostic images of a patient (not shown in FIG. 1), which may be a human or animal patient. In embodiments, the imaging device 103 may be an x-ray computed tomography (CT) imaging device. The patient may be positioned within a central bore 107 of the imaging device 103 and an x-ray source and detector may be rotated around the bore 107 to obtain x-ray image data (e.g., raw x-ray projection data) of the patient. The collected image data may be processed using a suitable processor (e.g., computer) to perform a three-dimensional reconstruction of the object. In other embodiments, the imaging device 103 may comprise one or more of an x-ray fluoroscopic imaging device, a magnetic resonance (MR) imaging device, a positron emission tomography (PET) imaging device, a single-photon emission computed tomography (SPECT), or an ultrasound imaging device. In embodiments, image data may be obtained pre-operatively (i.e., prior to performing a surgical procedure), intra-operatively (i.e., during a surgical procedure) or post-operatively (i.e., following a surgical procedure) by positioning the patient within the bore 107 of the imaging device 103. In the system 100 of FIG. 1, this may be accomplished by moving the imaging device 103 over the patient to perform a scan while the patient may remain stationary.

Examples of x-ray CT imaging devices that may be used according to various embodiments are described in, for example, U.S. Pat. No. 8,118,488, U.S. Patent Application Publication No. 2014/0139215, U.S. Patent Application Publication No. 2014/0003572, U.S. Patent Application Publication No. 2014/0265182 and U.S. Patent Application Publication No. 2014/0275953, the entire contents of all of which are incorporated herein by reference. In the embodiment shown in FIG. 1, the patient support 60 (e.g., surgical table) upon which the patient may be located is secured to the imaging device 103, such as via a column 50 which is mounted to a base 20 of the imaging device 103. A portion of the imaging device 103 (e.g., an O-shaped imaging gantry 40) which includes at least one imaging component may translate along the length of the base 20 on rails 23 to perform an imaging scan of the patient, and may translate away from the patient to an out-of-the-way positon for performing a surgical procedure on the patient.

An example imaging device 103 that may be used in various embodiments is the AIRO® intra-operative CT system manufactured by Mobius Imaging, LLC and distributed by Brainlab, AG. Other imaging devices may also be utilized. For example, the imaging device 103 may be a mobile CT device that is not attached to the patient support 60 and may be wheeled or otherwise moved over the patient and the support 60 to perform a scan. Examples of mobile CT devices include the BodyTom® CT scanner from Samsung Electronics Co., Ltd. and the O-arm® surgical imaging system form Medtronic, plc. The imaging device 103 may also be a C-arm x-ray fluoroscopy device. In other embodiments, the imaging device 103 may be a fixed-bore imaging device, and the patient may be moved into the bore of the device, either on a surgical support 60 as shown in FIG. 1, or on a separate patient table that is configured to slide in and out of the bore. Further, although the imaging device 103 shown in FIG. 1 is located close to the patient within the surgical theater, the imaging device 103 may be located remote from the surgical theater, such as in another room or building (e.g., in a hospital radiology department).

The motion tracking system 105 shown in FIG. 1 includes a plurality of marker devices 119, 202 and an optical sensor device 111. Various systems and technologies exist for tracking the position (including location and/or orientation) of objects as they move within a three-dimensional space. Such systems may include a plurality of active or passive markers fixed to the object(s) to be tracked and a sensing device that detects radiation emitted by or reflected from the markers. A 3D model of the space may be constructed in software based on the signals detected by the sensing device.

The motion tracking system 105 in the embodiment of FIG. 1 includes a plurality of marker devices 119, 202 and a stereoscopic optical sensor device 111 that includes two or more cameras 206 (e.g., IR cameras). The optical sensor device 111 may include one or more radiation sources (e.g., diode ring(s)) that direct radiation (e.g., IR radiation) into the surgical field, where the radiation may be reflected by the marker devices 119, 202 and received by the cameras. The marker devices 119, 202 may each include three or more (e.g., four) reflecting spheres, which the motion tracking system 105 may use to construct a coordinate system for each of the marker devices 119, 202. A computer 113 may be coupled to the sensor device 111 and may determine the transformations between each of the marker devices 119, 202 and the cameras using, for example, triangulation techniques. A 3D model of the surgical space in a common coordinate system may be generated and continually updated using motion tracking software implemented by the computer 113. In embodiments, the computer 113 may also receive image data from the imaging device 103 and may register the image data to the common coordinate system as the motion tracking system 105 using image registration techniques as are known in the art.

In embodiments, at least one reference marker device may be attached to the patient, as described further below. The patient reference marker device may be rigidly attached to a landmark in the anatomical region of interest (e.g., clamped or otherwise attached to a bony portion of the patient's anatomy) to enable the anatomical region of interest to be continually tracked by the motion tracking system 105. The patient reference marker device may be used to define the common, patient-based coordinate system during the procedure. Additional marker devices 119 may be attached to surgical tools or instruments 104 to enable the tools/instruments 104 to be tracked within the common coordinate system. Another marker device 202 may be rigidly attached to the robotic arm 101, such as on the end effector 102 of the robotic arm 101, to enable the position of robotic arm 101 and end effector 102 to be tracked using the motion tracking system 105. The computer 113 may also include software configured to perform a transform between the joint coordinates of the robotic arm 101 and the common coordinate system of the motion tracking system 105, which may enable the position and orientation of the end effector 102 of the robotic arm 101 to be controlled with respect to the patient 200.

In addition to passive marker devices described above, the motion tracking system 105 may alternately utilize active marker devices that may include radiation emitters (e.g., LEDs) that may emit radiation that is detected by an optical sensor device 111. Each active marker device or sets of active marker devices attached to a particular object may emit radiation in a pre-determined strobe pattern (e.g., with modulated pulse width, pulse rate, time slot and/or amplitude) and/or wavelength which may enable different objects to be uniquely identified and tracked by the motion tracking system 105. One or more active marker devices may be fixed relative to the patient, such as secured to the patient's skin via an adhesive membrane or mask. Additional active marker devices may be fixed to surgical tools 104 and/or to the end effector 102 of the robotic arm 101 to allow these objects to be tracked relative to the patient.

In further embodiments, the marker devices may be passive maker devices that include moird patterns that may enable their position and orientation to be tracked in three-dimensional space using a single camera using Moird Phase Tracking (MPT) technology. Each moird pattern marker may also include a unique identifier or code that may enable different objects within the camera's field of view to be uniquely identified and tracked. Other tracking technologies, such as computer vision systems and/or magnetic-based tracking systems, may also be utilized.

As shown in FIG. 1, the optical sensor device 111 may include a plurality of cameras 206 mounted to an arm 208 extending above the patient surgical area. The arm 208 may be mounted to or above the imaging device 103. The arm 208 may enable the sensor device 111 to pivot with respect to the arm 208 and/or the imaging device 103 (e.g., via one or more ball joints 212). The arm 208 may enable a user to adjust the position and/or orientation of the sensor device 111 to provide the cameras 206 with a clear view into the surgical field while avoiding obstructions. The arm 208 may enable the position and/or orientation of the sensor device 111 to be adjusted and then locked in place during an imaging scan or surgical procedure.

The system 100 may also include at least one display device 120 as illustrated in FIG. 1. The display device 120 may display image data of the patient's anatomy obtained by the imaging device 103. In the case of CT image data, for example, the display device 120 may display a three-dimensional volume rendering of a portion of the patient's anatomy and/or may display two-dimensional slices (e.g., axial, sagittal and/or coronal slices) through the 3D CT reconstruction dataset. The display device 120 may facilitate planning for a surgical procedure, such as by enabling a surgeon to define one or more target positions in the patient's body and/or a path or trajectory into the patient's body for inserting surgical tool(s) to reach a target position while minimizing damage to other tissue or organs of the patient. The position and/or orientation of one or more objects tracked by the motion tracking system 105 may be shown on the display 120, and may be shown overlaying the image data. The use of tracked surgical instruments or tools in combination with pre-operative or intra-operative images of the patient's anatomy in order to guide a surgical procedure may be referred to as "image-guided surgery."

In embodiments, the display device 120 may be a handheld display device, such as a tablet computer device. One or more handheld display devices 120 may be mounted to an arm 208 extending above the patient surgical area, as shown in FIG. 1. The arm 208 may also support the optical sensing device 111 for the motion tracking system 105, as described above. The one or more display devices 120 may be suspended from the arm 208, and the position of a display device 120 may be adjustable along the length of the arm 208. In other embodiments, a handheld display device 120 may be mounted to the patient support 60 or column 50 or to any portion of the imaging system 103, or to any of the wall, ceiling or floor in the operating room, or to a separate cart. Alternately or in addition, the at least one display device 120 may be a monitor display that may be located on a mobile cart or mounted to another structure (e.g., a wall) within the surgical theater.

As shown in FIG. 1, the robotic arm 101 may be fixed to the imaging device 103, such as on a support element 214 (e.g., a curved rail) that may extend concentrically over the outer surface of the O-shaped gantry 40 of the imaging device 103. In embodiments, an arm 208 to which the optical sensing device 111 is mounted may be mounted to the same or a similar support element 214 (e.g., curved rail) as the robotic arm 101. The position of the robotic arm 101 and/or the arm 208 may be adjustable along the length of the support element 214. In other embodiments, the robotic arm 101 may be secured to any other portion of the imaging device 103, such as directly mounted to the gantry 40. Alternatively, the robotic arm 101 may be mounted to the patient support 60 or column 50, to any of the wall, ceiling or floor in the operating room, or to a separate cart. In further embodiments, the robotic arm 101 and/or the optical sensing device 111 may be mounted to a separate mobile shuttle, as described in U.S. Provisional Application No. 62/395,443, filed on Sep. 16, 2016, which is incorporated by reference herein. Although a single robotic arm 101 is shown in FIG. 1, it will be understood that two or more robotic arms 101 may be utilized. In addition, various embodiments of a computer-assisted surgical method or system may include image-guided or navigation-supported surgery without the use of a robotic arm 101.

The at least one robotic arm 101 may aid in the performance of a surgical procedure, such as a minimally-invasive spinal surgical procedure or various other types of orthopedic, neurological, cardiothoracic and general surgical procedures. In embodiments, the motion tracking system 105 may track the position of the robotic arm 101 (e.g., via marker device 202 on end effector 102 as shown in FIG. 1) within the patient coordinate system. A control loop may continuously read the tracking data and the current parameters (e.g., joint parameters) of the robotic arm 101 and may send instructions to a robotic controller to cause the robotic arm 101 to move to a desired position and orientation within the patient coordinate system.

In embodiments, a surgeon may use an image-guided surgery system as a planning tool for a surgical procedure, such as by setting trajectories within the patient for inserting surgical tools, as well as by selecting one or more target locations for a surgical intervention within the patient's body. The trajectories and/or target locations set by the surgeon may be saved (e.g., in a memory of a computer device, such as computer device 113 shown in FIG. 1) for later use during surgery. In embodiments, the surgeon may be able to select stored trajectories and/or target locations using an image guided surgery system, and the robotic arm 101 may be controlled to perform a particular movement based on the selected trajectory and/or target location. For example, the robotic arm 101 may be moved to position the end effector 102 of the robotic arm 101 into alignment with the pre-defined trajectory and/or over the pre-determined target location. The end effector 102 may include a hollow tube or cannula which may be used to guide an instrument 104 into the patient's body along the pre-defined trajectory and/or to the pre-defined target location. Alternately, the end effector 102 itself may be or may include an instrument that may be inserted into the patient's body and guided along the pre-defined trajectory and/or to the pre-defined target location.

Various embodiments include methods and systems for attaching a reference marker to a patient in a computer-assisted image-guided surgery system. As discussed above, a reference marker device (e.g., reference arc) may be rigidly attached to a landmark in the anatomical region of interest (e.g., clamped or otherwise attached to a bony portion of the patient's anatomy) to enable the anatomical region of interest to be continually tracked by the motion tracking system 105. During an image guided surgical procedure, the diagnostic imaging data of the relevant anatomy may be registered to a patient coordinate system based on the position and orientation of the reference marker device 115, which may be continually tracked by the motion tracking system 105. The registration may become inaccurate, however, if a marker device is not rigidly fixed to the patient and/or is accidentally bumped causing it to change its position relative to the patient during a surgical procedure. In some situations, the surgeon may not be aware that the marker device has moved relative to the patient and that the image registration is no longer accurate.

Figure 2A:
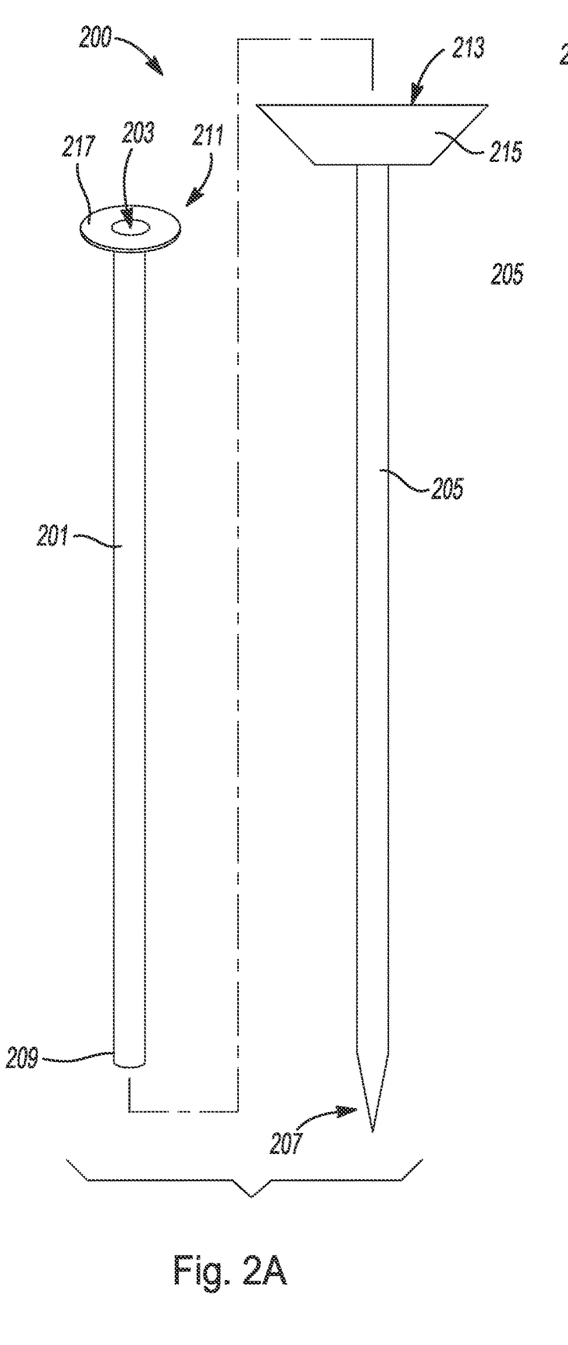
FIGS. 2A-2D illustrate a first embodiment apparatus for attaching a reference marker to a patient.
Figure 2B:
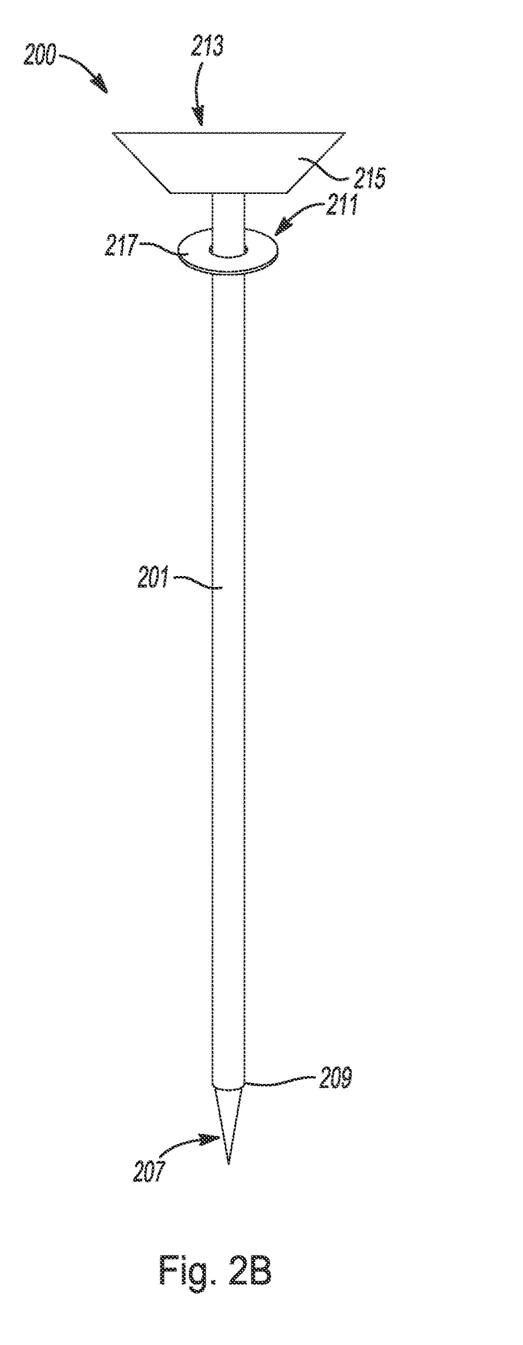

A first embodiment of an apparatus 200 for attaching a reference marker to a patient is shown in FIGS. 2A-2D. The apparatus 200 includes an outer cannula 201 with a hollow interior 203. An elongated member 205 having a sharp tip end 207 may be insertable within the outer cannula 201. FIG. 2A illustrates the elongated member 205 outside of the outer cannula 201 and FIG. 2B illustrates the elongated member 205 inserted within the outer cannula 201. When the elongated member 205 is inserted in the outer cannula 201 as shown in FIG. 2B, the sharp tip end 207 may project beyond a first end 209 (e.g., tip end) of the cannula 201. The sharp tip end 207 may be a cortical perforator that is configured to break through the cortical surface of a bone to enable the apparatus 200 to be advanced into the bone. The elongated member 205 may be attached to the outer cannula 201 when it is inserted, such as via a threaded connector at the second ends 211, 213 of the cannula 201 and the elongated member 205. As shown in FIGS. 2A-2B, the elongated member 205 may optionally include a handle 215 (e.g., a t-handle) at the second end 213 of the elongated member 205. The apparatus as shown in FIG. 2B may be inserted into a patient such that the tip end of the apparatus passes through the patient's skin and punctures the outer cortical surface of a bone. After puncturing the cortical surface, the elongated member 205 may optionally be disengaged from the outer cannula 201 (e.g., via the threaded connector) and may be removed from the outer cannula 201. The outer cannula 201 may be advanced further into the interior portion of the bone. The outer cannula 201 may include a flange 217 or other feature (e.g., a t-handle) to enable the user to grip and push the outer cannula 201 into the bone.

In some embodiments, the apparatus 200 may be a biopsy needle, including a bone marrow biopsy needle (e.g., a Jamshidi™ needle). The apparatus 200 may optionally be used to harvest tissue from the patient, and in particular may be used to harvest bone marrow from the patient. The obtained bone marrow cells may be used to promote bone growth in a spinal fusion or other surgical treatment of the patient. In one example, the outer cannula 201 may be pushed into the interior portion of the bone containing the marrow while optionally rotating the outer cannula 201 in order to collect the marrow within the hollow interior 203 of the cannula 201. The sample (e.g., core) containing the marrow may then be removed from the outer cannula 201, such as by aspiration or by inserting a separate instrument (e.g., a marrow acquisition cradle) into the cannula 201 to collect the sample.

Figure 3A:
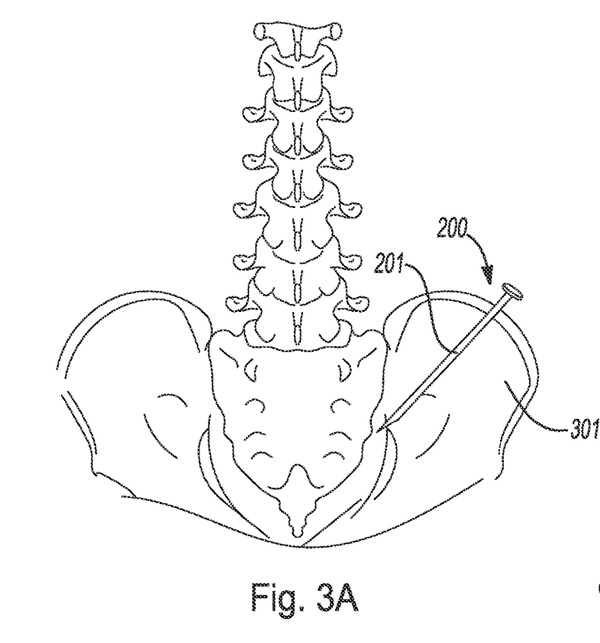
FIGS. 3A-3C schematically illustrate an embodiment apparatus embedded within a bone of a patient.
Figure 3B:
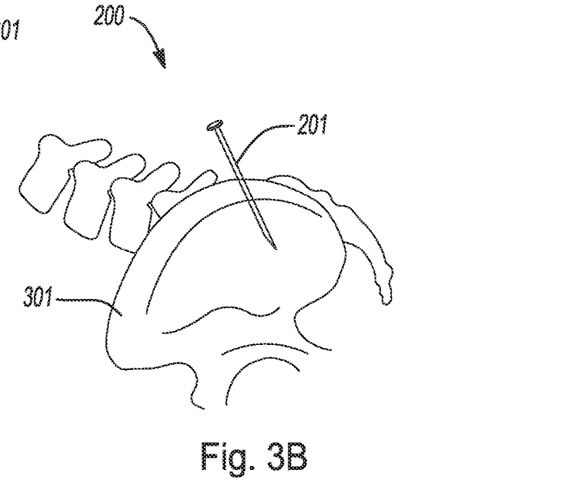

In various embodiments, the apparatus 200 shown in FIGS. 2A-2B may be inserted into the iliac crest of the patient. This is schematically illustrated in FIGS. 3A-3B, which are anterior and lateral views showing an outer cannula 201 of an embodiment apparatus 200 embedded within the iliac crest 301 of a patient. It will be understood that the apparatus 200 may be inserted into another bone or skeletal structure of a patient. In general, the apparatus 200 may be inserted into a structure that is relatively proximate (e.g., less than about 1 meter) from a site requiring surgical intervention.

Figure 2C:
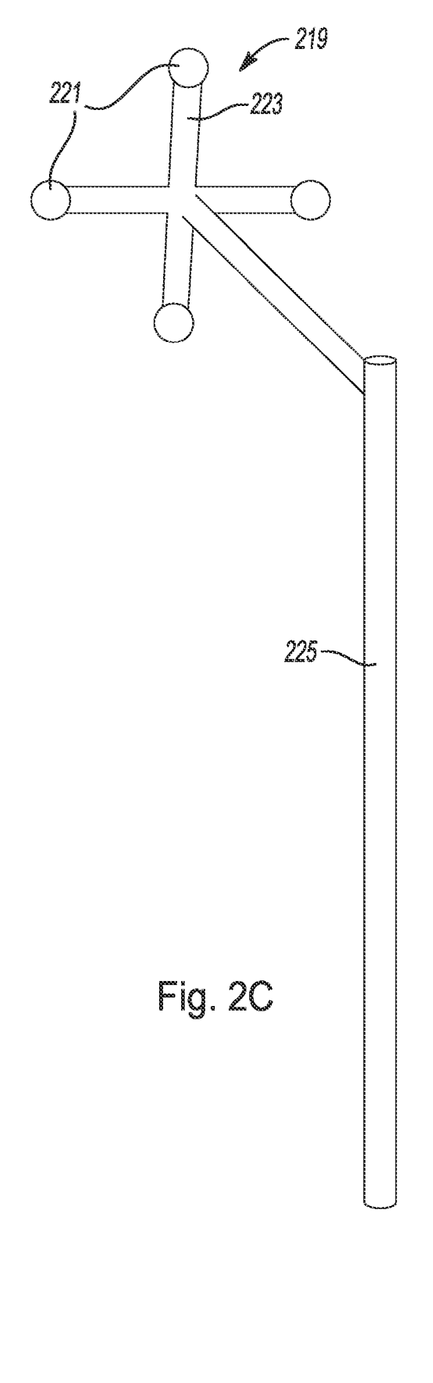
Figure 2D:
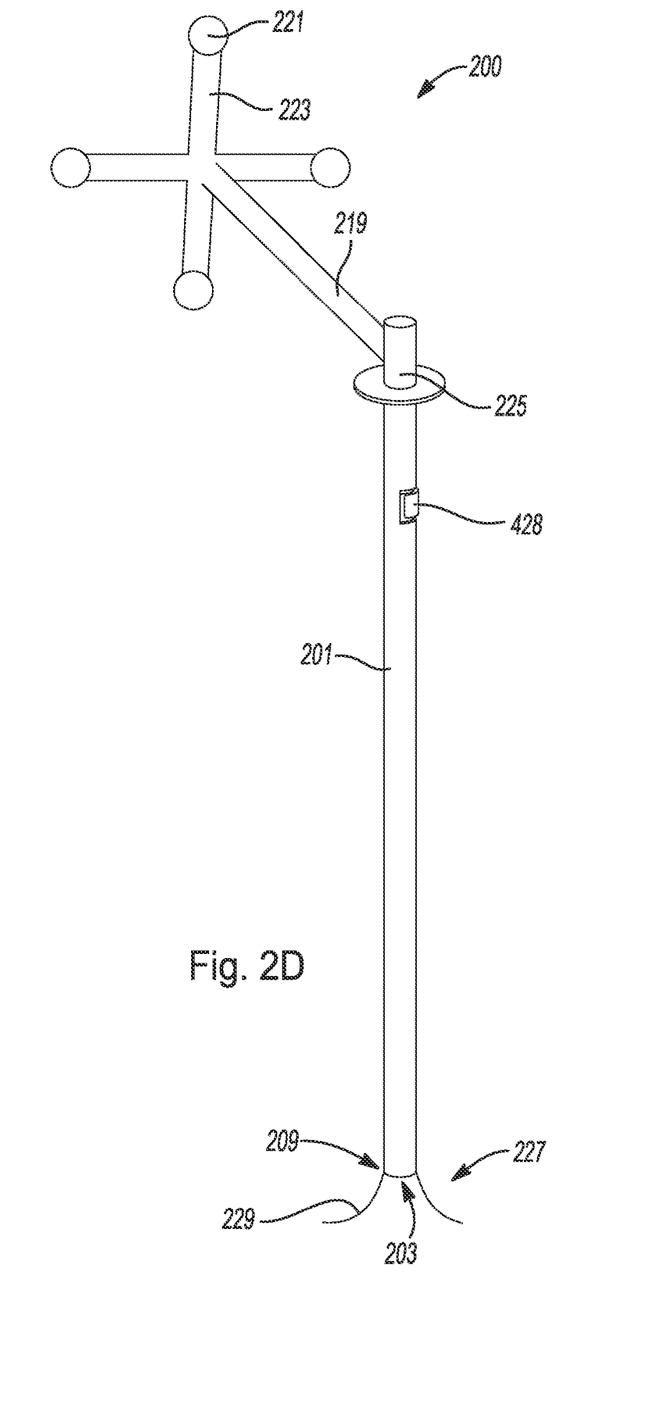
Figure 3C:
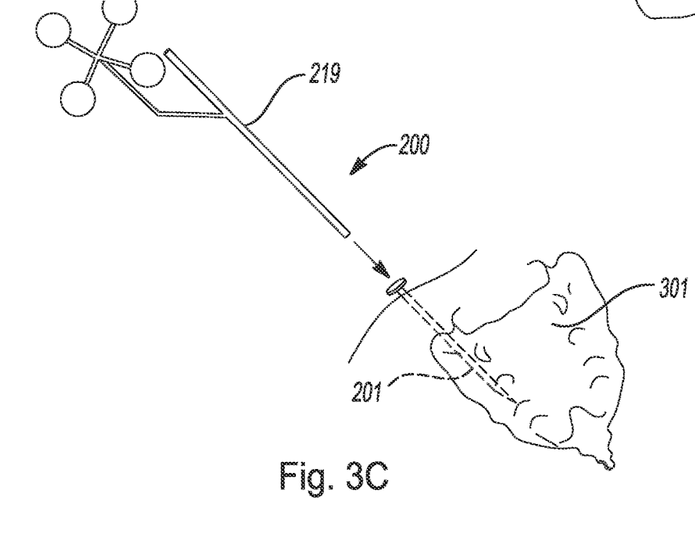

The apparatus 200 also includes a marker device 219 that may be fixed to the outer cannula 201. In one embodiment, as shown in FIG. 2C, the marker device 219 may include a plurality of optical markers 221 (e.g., reflective spheres) arrayed on a rigid-frame 223. The optical markers 221 may be arranged in a unique pattern on the frame 223 to enable the array of markers 221 to be identified and tracked by a motion tracking system 105 as described above with reference to FIG. 1. The frame 223 may be attached to an elongated member 225 that may be sized and shaped to be inserted into the outer cannula 201. FIG. 2D illustrates the marker device 219 with the elongated member 225 inserted into the outer cannula 201. The marker device 219 may be locked to the cannula 201 using a suitable attachment mechanism, such as a threaded connector, a latch mechanism, a locking collar, a snap-fit connector, an interference-fit, etc. FIG. 3C illustrates the marker device 219 being inserted into an outer cannula 201 that is partially embedded within the bone 301 of a patient.

The apparatus may optionally also include an anchoring device 227 that prevents the apparatus 200 from moving relative to patient, including rotational movement of the apparatus 200 about the central axis of the outer cannula 201. The anchoring device 227 may include a plurality of elements that may extend from the outer cannula 201 to fix the apparatus 200 within the surrounding bone structure. In embodiments, the anchoring device 227 may be selectively deployed after the outer cannula 201 is at a desired position within the bone of the patient. For example, the anchoring device 227 may be deployed by extending a plurality of anchoring elements radially outward with respect to the outer surface of the cannula 201 and/or longitudinally away from the tip end 209 of the cannula 201 in order to anchor the apparatus 200 within the bone and inhibit relative movement of the apparatus 200 and bone.

In one embodiment shown in FIG. 2D, the anchoring device 227 comprises a plurality of wires 229 that extend from the tip end 209 of the outer cannula 201. The wires 229 may extend into the relatively softer (i.e., cancellous) bone tissue in the interior of the patient's bone to anchor the apparatus 200 within the bone. Although the embodiment shown in FIG. 2D illustrates two wires 229 extending from the outer cannula 201, it will be understood that an anchoring device 227 may include a different number of wires 229. Further, as an alternative and/or in addition to wires 229 as shown in FIG. 2D, the anchoring device 227 may comprise one or more of a burr, a cleat, and expandable cage or other member that extends from the cannula 201 to help anchor the apparatus 200 within the patient's bone.

The anchoring device 227 is preferably comprised of a bio-compatible material, such as a nickel-titanium (nitinol) alloy. In some embodiments, the anchoring device 227 may be composed of a shape memory alloy, such as nitinol, and may be manufactured to a body temperature response so that the anchoring device 227 assumes a pre-determined austenitic shape within the patient's body. The pre-determined austenitic shape may be configured to aid in the anchoring of the apparatus 200 when the apparatus 200 is inserted into the patient's bone.

In some embodiments, the anchoring device 227, such as wires 229, may be located on or within the outer cannula 201 of the apparatus 200. For example, the anchoring device 227 (e.g., wires 229) may be attached to the outer surface of the cannula 201 and may extend out from the cannula 201 when the cannula 201 is inserted into a bone. In further embodiments, the anchoring device 227 (e.g., wires 229) may be located within the cannula, such as within the central opening 203 of the cannula 201 or within one more housings formed within the sidewall of the cannula 201. The anchoring device 227 may be deployed by pushing the anchoring device 227 (e.g. wires 229) out through the tip end 209 of the cannula 201 such that the anchoring device 227 may extend into the surrounding bone tissue.

In some embodiments, the anchoring device 227 may be deployed using a mechanical actuator 428, such as a button, a rotatable handle or knob, or a mechanical slide, that is coupled to the anchoring device 227 and enables a user to cause the anchoring device 227 to extend into the surrounding bone tissue. The mechanical actuator 428 may be a spring-loaded actuator that causes the anchoring device 227 (e.g., wires 229) to project out from the tip end 209 of the cannula 201 and into the surrounding tissue. In some embodiments, the anchoring device 227 may deploy automatically when the marker device 219 is inserted within the outer cannula 201. For example, the marker device 219 may include feature(s) that engage with and push down on the anchoring device 227 as the marker device 219 is inserted, causing the anchoring device 217 to extend out from the tip end 209 of the outer cannula 201. In some embodiments, inserting the marker device 219 may engage a triggering device (e.g., a spring-loaded actuator) that causes the anchoring device 217 to extend out from the outer cannula 201. The apparatus 200 may be configured such that the insertion of a different component into the outer cannula 201, such as the elongated member 205 of FIGS. 2A-2B, does not cause the anchoring device 227 to deploy.

In some embodiments, the anchoring device 227 (e.g., wires 229) may be located on the marker device 219, such as attached to the elongated member 225 shown in FIGS. 2C and 2D. Fully inserting the elongated member 225 into the outer cannula 201 may cause the anchoring device 227 to project out through the tip end 209 of the cannula 201 and extend into the surrounding bone tissue.

In embodiments, the anchoring device 227 may be retracted from the surrounding tissue before the apparatus 200 is removed from the patient. For example, the anchoring device 227 (e.g., wires 229) may be pulled into the outer cannula 201 using a mechanical actuator, or automatically by removing the marker device 219 from the cannula 201.

Figure 4:
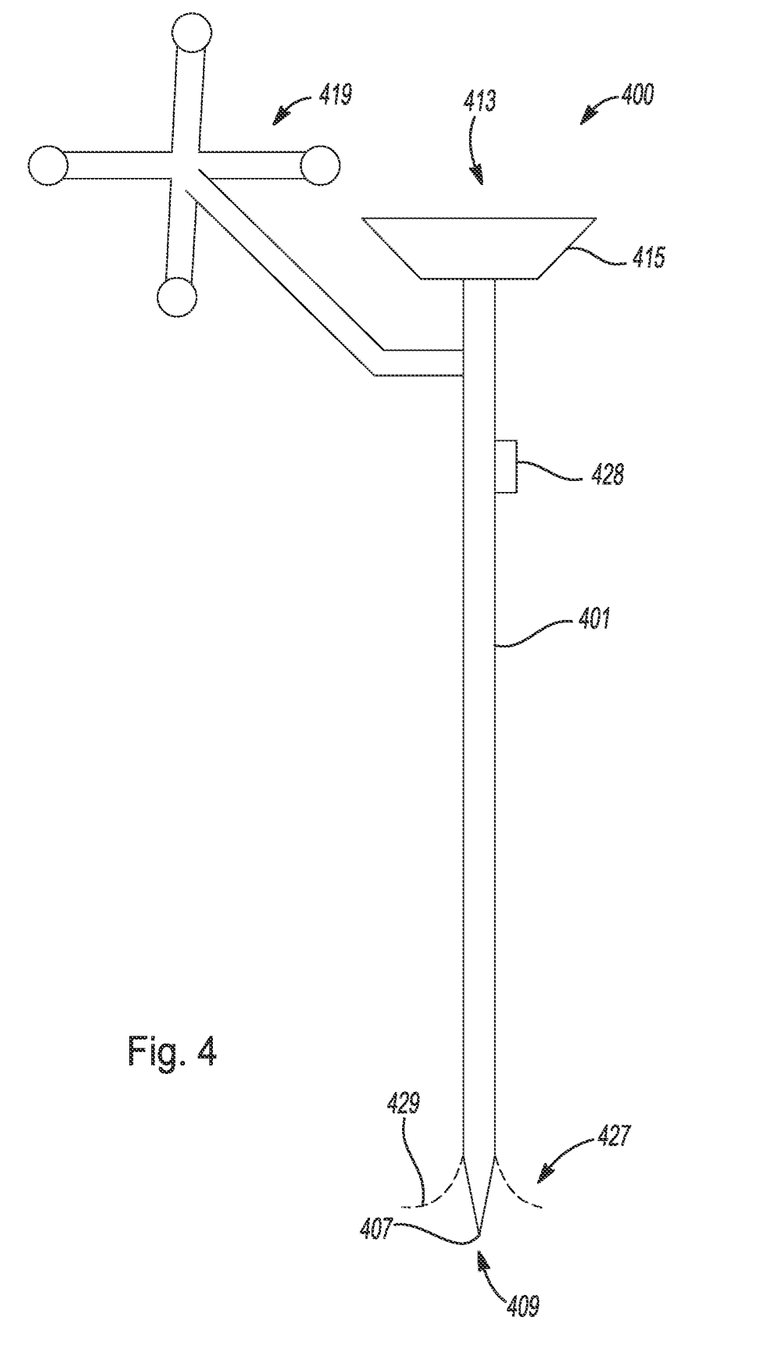
FIG. 4 illustrates a second embodiment apparatus for attaching a reference marker to a patient.

FIG. 4 illustrates another embodiment apparatus 400 for attaching a reference marker to a patient. Apparatus 400 is similar to apparatus 200 and includes an elongated member 401 (e.g., a rod) having a sharp tip 407 at a first end 409 of the apparatus 400. A handle 415 (e.g., a t-handle) may be located at a second end 413 of the apparatus 400. A marker device 419 is attached to the elongated member 401 near the second end 413 of the apparatus. The elongated member 401 may be a hollow cannula such as described above in reference to FIGS. 2A-2D, or may be a solid or partially solid rod that does not include a central opening extending through the elongated member 401. The marker device 419, handle 413 and/or sharp tip 407 may be non-removably attached to the elongated member 401.

The apparatus 400 may be inserted into a patient such that the sharp tip 407 pierces the skin and punctures the cortical surface of an underlying bone (e.g., the iliac crest). In embodiments, the user may continue to advance the sharp tip 407 into the interior portion of the bone to attach the apparatus 400 to the patient. Alternately, after puncturing the cortical surface, the sharp tip 407 may be retracted into the elongated member 401 (e.g., retracted into a housing located near the first end 409 of the elongated member 401, or pulled out through a central opening in the elongated member 401 similarly to the apparatus 200 described above). The elongated member 401 may be advanced into the interior of the bone with the sharp tip 407 removed or retracted. The apparatus 400 may optionally also include an anchoring device 427 (e.g., a plurality of wires 429, shown in phantom in FIG. 4) that may be deployed to anchor the apparatus 400 within the patient's bone. The anchoring device 427 may be selectively deployed using a trigger mechanism (e.g., a button 428).

Further embodiments include systems for performing image guided surgery that include multiple reference markers attached to a patient. Attaching multiple reference marker devices to the patient may provide redundancy such that if one marker device is not rigidly secured or becomes loose, any loss in the accuracy of the surgical navigation may be compensated for by one or more additional marker devices. The multiple marker devices may also be used to verify the accuracy of the patient registration, and in some cases, may enable a registration correction to be performed without needing to re-scan the patient using an imaging device.

Figure 5:
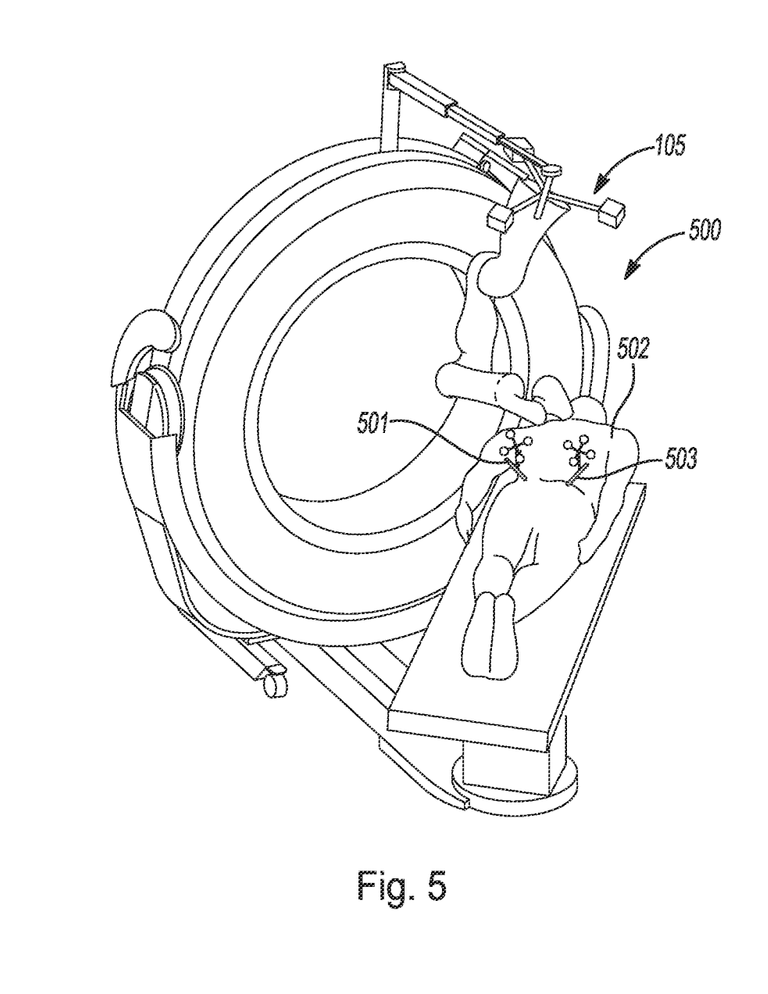
FIG. 5 illustrates an embodiment system for performing image guided surgery that includes a plurality of reference markers fixed to a patient.

FIG. 5 illustrates an embodiment system 500 for performing image guided surgery (IGS) that includes two reference markers 501, 503 attached to a patient 502. The two reference markers 501, 503 may each comprise an apparatus 200, 400 such as described above in connection with FIGS. 2A-4, and may be embedded within different bone structures of the patient 502 (e.g., the left and right iliac crests). Although two reference markers 501, 503 are shown in FIG. 5, it will be understood that a greater number (e.g., 3, 4, 5, etc.) of reference markers may be utilized.

During image guided surgery, representations of tracked objects may be displayed in conjunction with diagnostic images obtained using an imaging device 103 (e.g., a CT scanner) in a patient-based coordinate system that may be based on the location(s) of reference marker 501 and/or reference marker 503. In some embodiments, the patient-based coordinate system may be a blended or interpolated reference coordinate system that may be weighted by distance from the first and second reference marker devices 501, 503. Various embodiments for performing image guided surgery using multiple reference markers attached to the patient are described in U.S. Provisional Application No. 62/385,552, filed Sep. 9, 2016, the entire contents of which are incorporated herein by reference.

The reference markers 501, 503 may be tracked by the motion tracking system 105 to detect a relative motion of reference markers 501, 503 during a surgical procedure. A detected relative motion between the markers may indicate that a reference marker 501, 503 is loose and/or has accidentally been bumped causing it to change its position relative to the patient during a surgical procedure. In such a case, the images displayed by the image guided surgery system may no longer accurately represent the current patient situation. In embodiments, the user may be notified (e.g., via an audible and/or visual alert) when there is a detected relative motion (e.g., greater than a pre-determined magnitude) between reference markers 501, 503. In some embodiments, the IGS software may be configured to determine which of the reference markers 501, 503 most likely moved relative to the patient (for example, where a first reference marker abruptly changes its position/orientation with respect to the camera position while a second marker's position/orientation with respect to the camera(s) remains constant, it is significantly more likely that the first marker has moved). In response to determining that a first reference marker has moved relative to the patient, the IGS may automatically perform surgical navigation within a coordinate system based on the location of the second marker device.

Figure 6:
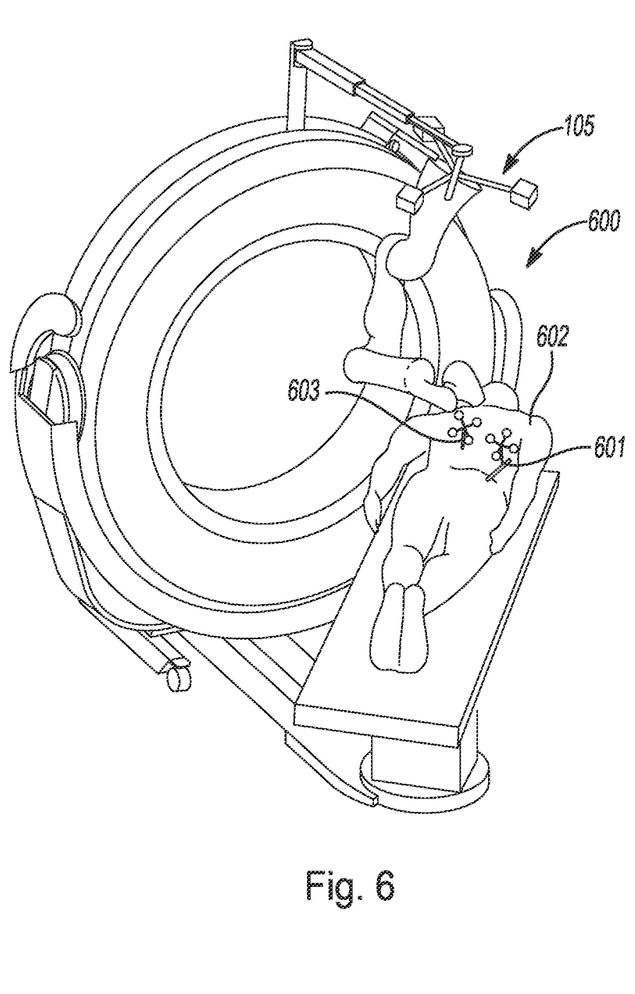
FIG. 6 illustrates another embodiment system for performing image guided surgery that includes a plurality of reference markers fixed to a patient

FIG. 6 illustrates a further embodiment system 600 for performing image guided surgery (IGS) that includes two reference markers 601, 603 attached to a patient 602. The two reference markers 601, 603 may be of different types and/or use different mechanisms for attaching to the patient. A first reference marker 601 may comprise an apparatus 200, 400 such as described above in connection with FIGS. 2A-4, and may be embedded within a first bone structure of the patient 602 (e.g., the iliac crest). One or more additional reference markers 603 may be attached to a different portion of the patient's skeletal structure, such as to a vertebra of the patient. The additional reference marker 603 may include a bone clamp that attaches to the spinous process, for example. The system 600 may otherwise be similar to system 500 as described above.

Figure 7:
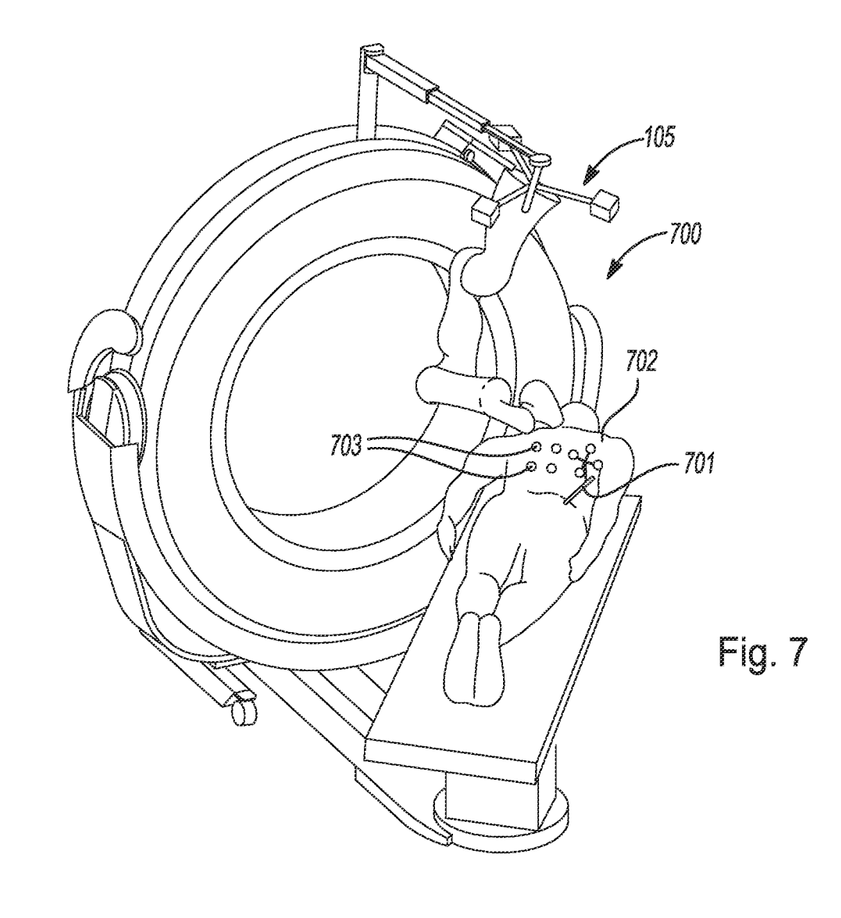
FIG. 7 illustrates yet another embodiment system for performing image guided surgery that includes a first reference marker fixed to a bone of a patient and a plurality of optical markers fixed over the skin surface of the patient.

FIG. 7 illustrates yet another embodiment system 700 for performing image guided surgery (IGS). In this embodiments, a reference marker 701 may comprise an apparatus 200, 400 such as described above in connection with FIGS. 2A-4, and may be embedded within a first bone structure of the patient 702 (e.g., the iliac crest). A plurality of optical markers 703 (e.g., reflective spheres) may be attached over the skin surface of the patient 702. The optical markers 703 may be attached using an adhesive. The plurality of optical markers 703 may at least partially surround the surgical area.

Reference marker 701 may be rigidly fixed to the patient's bone, while the additional optical markers 703 in this embodiment are attached to soft tissue of the patient and may have a limited degree of motion (e.g., both absolute motion relative to the anatomic region of interest and relative motion with respect to the other markers 703). Image registration and surgical navigation may utilize a patient-based coordinate system that may be based on the tracked position and orientation of the rigidly-attached reference marker 701. The additional optical markers 703 may also be tracked and may be used to verify that reference marker 701 has not moved with respect to the patient 702. For example, an average of the tracked positions of the additional optical markers 703 may be compared to the tracked position of reference marker 701. Where the reference marker 703 is determined to have moved in a particular direction and/or by a particular magnitude with respect to the average position of markers 703, this may indicate that the reference marker 701 has moved relative to the patient 702. The user may be notified (e.g., via an audible and/or visual alert) when it is determined that the reference marker 701 has moved.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. An apparatus for attaching a reference marker device to a patient, comprising:
    an elongated member extending along an axis between a first end and a second end;
    at least one marker operatively attached to the elongated member to enable the apparatus to be tracked using a motion tracking system;
    a sharp tip located proximate to the first end of the elongated member that is configured to break through a cortical surface of a bone of the patient to enable the elongated member to be advanced into the bone; and
    an anchoring device extending from the elongated member in a direction transverse to the axis to anchor the apparatus within the bone and inhibit rotation of the apparatus about the axis relative to the bone.

2. The apparatus of claim 1, wherein the elongated member comprises a cannula having a central opening extending between a first end and a second end of the cannula.

3. The apparatus of claim 2, further comprising a second elongated member having a first end and a second end, the sharp tip being located at the first end of the elongated member, the second elongated member being insertable into the cannula, such that the sharp tip extends beyond the first end of the cannula.

4. The apparatus of claim 3, further comprising a connector for connecting the cannula and the second elongated member at their respective second ends.

5. The apparatus of claim 3, wherein the second elongated member is removable from the cannula.

6. The apparatus of claim 5, wherein the second elongated member is removable from the cannula after the sharp tip breaks through the cortical surface, and the cannula is configured collect bone tissue within the central opening of the cannula when the cannula is advanced into an interior portion of the bone.

7. The apparatus of claim 6, wherein the bone tissue is removable through the second end of the cannula to harvest bone marrow of the patient.

8. The apparatus of claim 5, further comprising:
    a third elongated member that is insertable into the cannula, the reference marker device being attached to the third elongated member.

9. The apparatus of claim 8, wherein the anchoring device deploys automatically when the third elongated member is inserted into the cannula.

10. The apparatus of claim 8, further comprising an attachment mechanism to lock the third elongated member within the cannula.

11. The apparatus of claim 1, wherein the anchoring device is deployed by extending a plurality of anchoring elements radially outward with respect to an outer surface of the elongated member and/or longitudinally away from the first end of the elongated member.

12. The apparatus of claim 1, wherein the anchoring device comprises a plurality of wires that are extendable from the first end of the elongated member.

13. The apparatus of claim 12, wherein the anchoring device is composed of a shape-memory alloy.

14. The apparatus of claim 12, wherein the anchoring device comprises a nickel titanium alloy.

15. The apparatus of claim 12, further comprising an actuator for selectively deploying the anchoring device.

16. The apparatus of claim 1, wherein the bone is an iliac crest of the patient.

17. The apparatus of claim 1, wherein the reference marker device is non-removably attached to the elongated member.

18. The apparatus of claim 1, wherein the at least one marker comprises a plurality of reflective spheres mounted to a rigid frame.

* * * * *